(12) United States Patent
Sabater-Lüntzel et al.

(10) Patent No.: US 6,303,173 B1
(45) Date of Patent: Oct. 16, 2001

(54) FRAGRANCE AND FLAVOR MATERIAL

(75) Inventors: Christopher Sabater-Lüntzel, Höxter; Sabine Widder, Holzminden; Wilhelm Pickenhagen, Höxter, all of (DE)

(73) Assignee: Dragoco Gerberding & Co. AG (DE)

( * ) Notice: Subject to any disclaimer, the term of this patent is extended or adjusted under 35 U.S.C. 154(b) by 0 days.

(21) Appl. No.: 09/378,401

(22) Filed: Aug. 20, 1999

(30) Foreign Application Priority Data

Aug. 20, 1998 (DE) ................................. 198 37 702

(51) Int. Cl.⁷ ............................. A23L 1/22; C07C 315/00
(52) U.S. Cl. ..................... 426/535; 426/534; 426/650; 568/18
(58) Field of Search ..................... 426/534, 535, 426/650; 568/18, 61, 62

(56) References Cited

U.S. PATENT DOCUMENTS 5,493,060 * 2/1996 Rubino et al. ..................... 568/721

* cited by examiner

*Primary Examiner*—Leslie Wong
(74) *Attorney, Agent, or Firm*—Pendorf & Cutliff

(57) ABSTRACT

Described are compounds of the general formula A

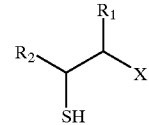

where

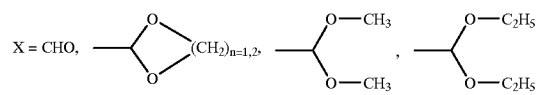

$R_2$=$CH_3$, $C_2H_5$, $C_3H_7$ (n, iso) or $C_4H_9$ (n, iso, tert) and
$R_2$=$CH_3$, $C_2H_5$, $C_3H_7$ (n, iso) or $C_4H_9$ (n, iso, tert)

which are especially useful as fragrance or flavor materials. The 3-mercapto-2-alkyl-alkanals of the general formula A in which X—CHO are formed by reaction of the corresponding 2-alkyl-2-alkenals with hydrogen sulfide.

5 Claims, 4 Drawing Sheets

```
File       :
Operator   :
Acquired   : 16 Jun 98  12:04 pm using AcqMethod WAXSL
Instrument :    GCD
Sample Name: 3-Mercapto-2-methyl-pentanal
Misc Info  : KAS 60-12-240(5); Li67,02; 0,5µl/sl
Vial Number: 1
```
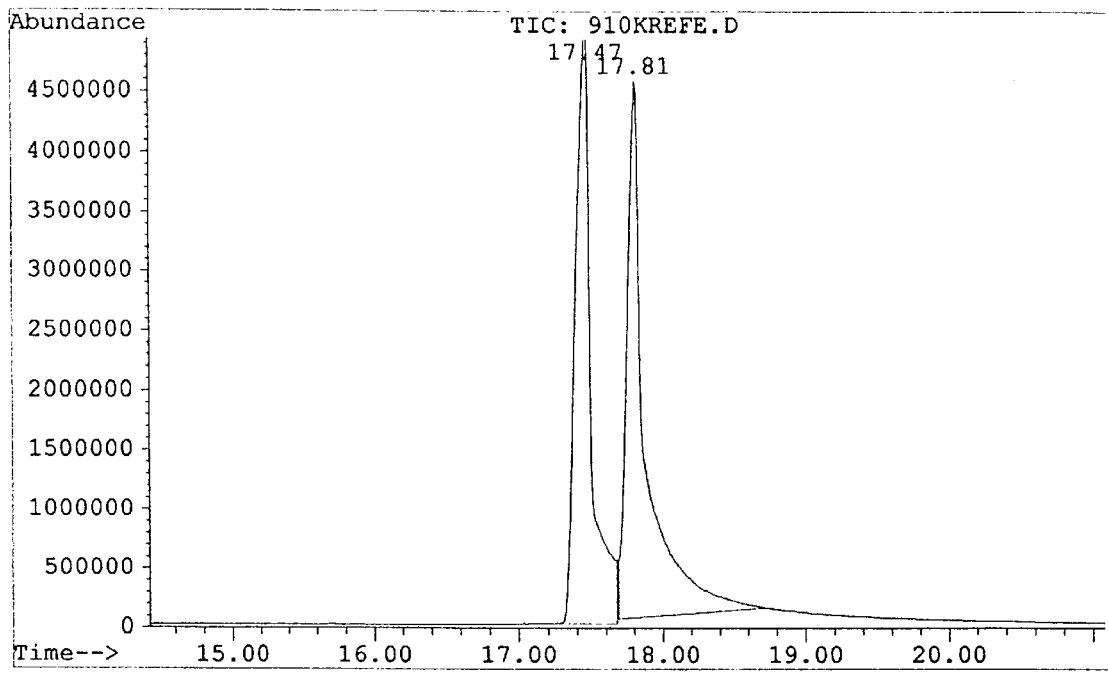
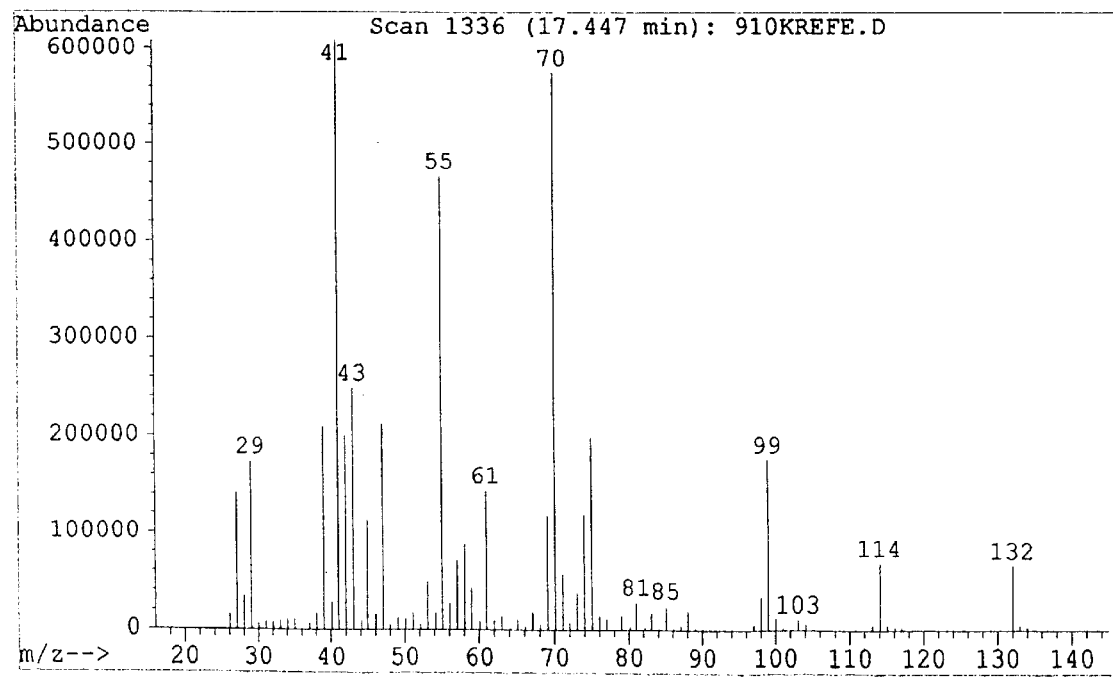
Fig. 3

```
Operator    :
Acquired    : 16 Jun 98  12:04 pm using AcqMethod WAXSL
Instrument  :    GCD
Sample Name: 3-Mercapto-2-methyl-pentanal
Misc Info   : KAS 60-12-240(5); Li67,02; 0,5µl/sl
Vial Number: 1
```
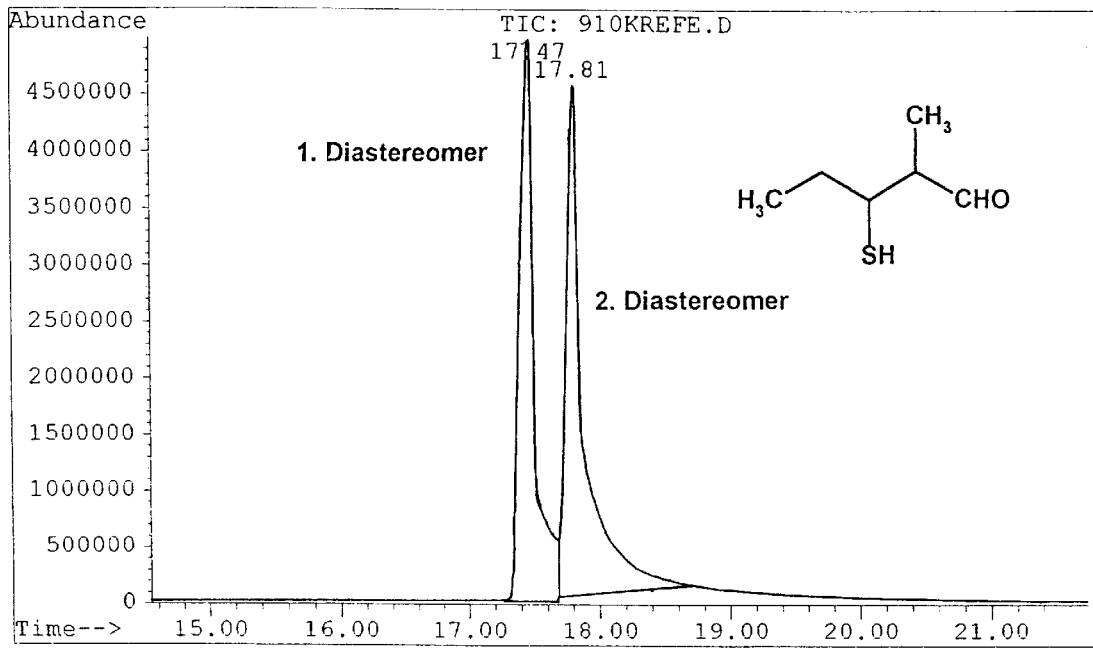
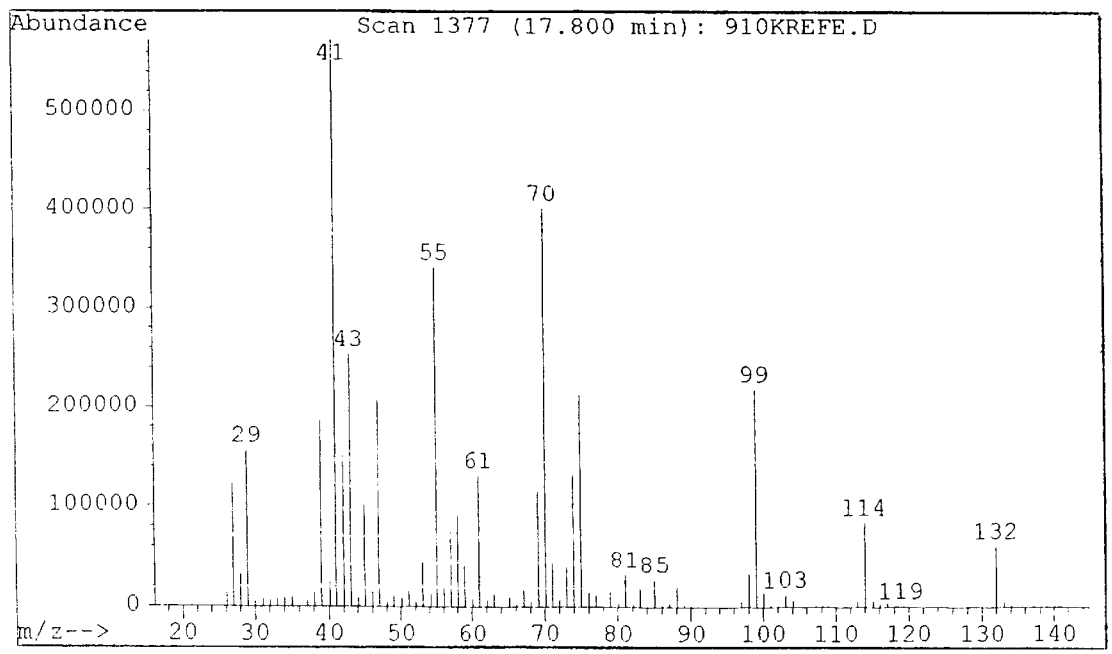
Fig. 4

FRAGRANCE AND FLAVOR MATERIAL

BACKGROUND OF THE INVENTION

1. Field of the Invention

The invention relates to a novel fragrance and flavor material and to a process for the preparation of this novel material.

2. Description of the Related Art

Foods are nowadays frequently flavored. This is because most consumers in modern industrialized societies expect a wide range of tasty foods at reasonable prices. The tastiness of food is very important since it generally brings about good digestibility. The flavoring industry has already made available a large number of flavors in order to make food available to and tasty for a large section of the population.

Flavor materials are used in order (a) to impart a taste note to food products which do not have their own taste, or (b) to compensate for losses in flavor which occur, for example, during the preparation process of a foodstuff.

SUMMARY OF THE INVENTION

The object of the present invention was to give a novel material for the flavoring of food (below also called "flavor material" for short), in particular a material with a meat flavor.

According to the invention, the following compounds of the general formula A

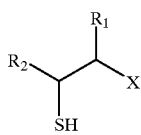

where

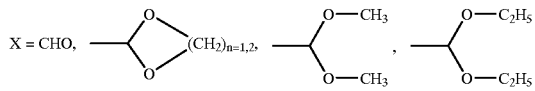

$R_1=CH_3$, $C_2H_5$, $C_3H_7$ (n, iso) or $C_4H_9$ (n, iso, tert) and $R_2=CH_3$, $C_2H_5$, $C_3H_7$ (n, iso) or $C_4H_9$ (n, iso, tert) are given as flavor material. This is because, surprisingly, it has been found that these newly synthesized compounds (aldehydes, e.g. 3-mercapto-2-methylpentanal, and acetals) are, even in low concentrations, highly suitable for giving foods (in particular meat broths or other meat dishes) an interesting odoriferous and gustatory note. Because the compounds according to the invention have a very high odoriferous and gustatory intensity, they can be used in large dilution; the person skilled in the art will adapt the exact concentrations or amounts for the flavoring of a foodstuff in the usual manner to the respective wishes and requirements of the individual case.

Moreover, the compounds according to the invention are also suitable for use as fragrance material, in particular as fragrance material in the perfume industry; they generally have a particularly low odor threshold value, which is proving advantageous since even small amounts of a compound according to the invention suffice to achieve a desired odor.

All the compounds according to the invention have the following structural features which, surprisingly, only produce the desired properties if they are present at the same time in a molecule:

an aldehyde or acetal function from the C-1,
a mercapto group (SH group) on the C-3 and
an alkyl radical on the C-2, i.e. chain branching.

In addition to the compounds according to the invention, the invention also relates to processes for their preparation.

In a process according to the invention for the preparation of a 3-mercapto-2-alkyl-alkanal of the formula A where X=CHO, $R_1=CH_3$, $C_2H_5$, $C_3H_7$ (n, iso) or $C_4H_9$ (n, iso, tert) and $R_2=CH_3$, $C_2H_5$, $C_3H_7$ (n, iso) or $C_4H_9$ (n, iso, tert), the corresponding 2-alkyl-2-alkenal is reacted with hydrogen sulfide.

And, finally, the invention also relates to flavored food with a content of one or more compounds according to the invention, and to the use of the compounds according to the invention as a fragrance or flavor material.

BRIEF DESCRIPTION OF THE DRAWINGS

For a fuller understanding of the nature and objects of the present invention reference should be made by the following detailed description taken in with the accompanying drawings in which:

FIGS. 1–4 are IR and NMR spectrum for 2-mercapto-2-methyl-pentan-1-ol produced in Example 1.

DETAILED DESCRIPTION OF THE INVENTION

Figure 1:
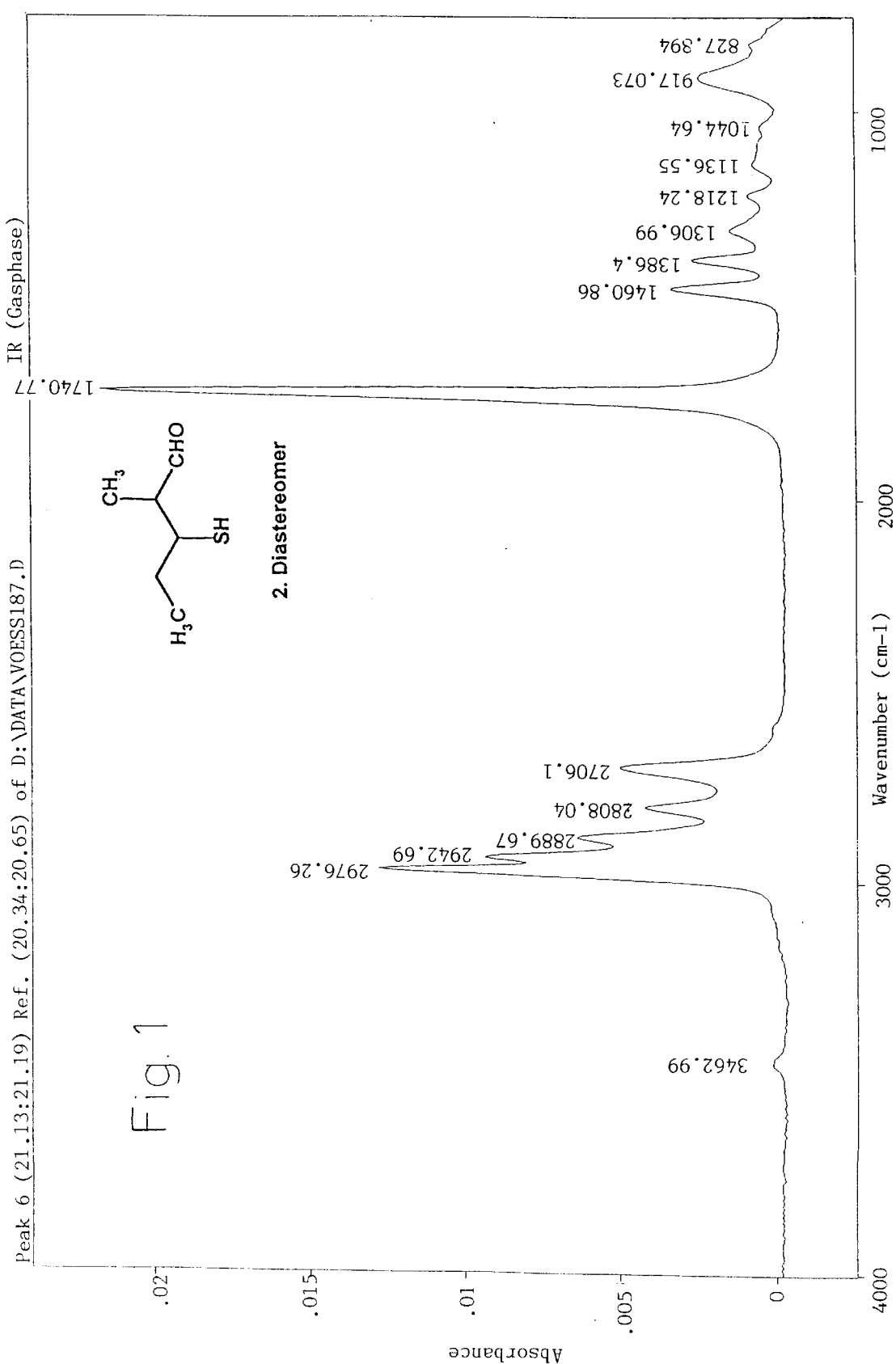

The aldehydes according to the invention (e.g. 3-mercapto-2-methyl-pentanal) are extremely interesting from a sensory point of view. They do, however, also have other properties which go beyond their purely odoriferous and gustatory properties.

For example, the aldehydes according to the invention, which are afterall substances which are relatively small in size, adhere to various surfaces—also in the mouth—for a surprisingly long time. This good adhesion (so called "long lasting") is demonstrated, for example, on a customary smell strip. Even days after a low-concentration solution of an aldehyde according to the invention (e.g. 3-mercapto-2-methylpentanal) has been applied to the smell strip, the particular odor of the aldehyde can be detected without trouble. This property is important particularly for the perfume industry since here there is a continuous need for novel and interesting compounds which adhere for a long time.

Another surprising effect which occurs when the aldehydes according to the invention are used is the so-called "mouthfeel". Particularly when the aldehydes according to the invention are used in meat flavor compositions they contribute to intensify the fullness, the volume and the body of the meat flavor. "Mouthfeel" properties normally occur only in substances which have a relatively high molecular weight, such as, for example, in pectins or starch products.

Instead of using the aldehydes according to the invention directly as fragrance or flavor material or as "mouthfeel" promoters, it is sometimes desirable to use chemical derivatives which, under the conditions of customary further processing—e.g. in an acidic medium, during boiling or roasting, in the air or similar—convert or can be converted into the respective aldehyde. The derivatives can themselves be interesting from a sensory point of view, (for example like the acetals according to the invention), but do not have to be.

The invention is described in more detail below by reference to examples:

EXAMPLE 1

Preparation of 3-mercapto-2-methylpentanal 321 g of freshly distilled 2-methyl-2-pentenal, 23 g of triethylamine and 1.8 g of hydroquinone are dissolved in 600 ml of dry tetrahydrofuran in a 500 ml stirrer heated to 40° C. and fitted with a gas inlet pipe. At 40° C., a vigorous stream of hydrogen sulfide is introduced over about 6 h. The hydrogen sulfide which escapes is absorbed by a downstream wash bottle containing sodium hydroxide solution. After the reaction, nitrogen is introduced through the reaction solution for 5 min in order to drive out excess hydrogen sulfide. The 3-mercapto-2-methylpentanal is isolated by washing the reaction solution with water and saturated sodium chloride solution, drying it over sodium sulfate and freeing it from solvent under a partial vacuum.

In the GC/MS analysis of the residue, the two diastereomer mercapto aldehydes are obtained in the ratio 1:1, as can be seen from the attached spectra (FIGS. 1–4)

Remarks

The 2-methyl-2-pentenal mentioned in Example 1 is commercially available. Other unsaturated precursor aldehydes, which have likewise been reacted to give aldehydes according to the invention but have not been mentioned individually here, are either likewise available commercially (e.g. 2,3-dimethylacrolein) or are readily accessible by known synthesis processes (α,β-unsaturated aldehydes by targeted aldol condensation: L. Brandsma, Preparative Polar Organometallic Chemistry 2, p. 145, Springer Verlag, Heidelberg 1990).

EXAMPLE 2

Preparation of 3-mercapto-2-alkylalkanal acetals (in particular 3-mercapto-2-methyl-pentanal acetals) using 2-(1,3-dioxolan-2-yl)pentane-3-thiol

2.1. Reaction of 2-methyl-2-pentenal with thioacetic acid to give 1-ethyl-2-methyl-3-oxopropyl thioacetate 9.8 g (0.1 mol) of 2-methyl-2-pentenal are introduced into a stirred apparatus, and, at 0° C. under a nitrogen atmosphere, 100 mg of piperidine are firstly added dropwise, and then 11.4 g (0.15 mol) of thioacetic acid are slowly added. The reaction mixture is then left to warm to room temperature and further stirred overnight. The reaction mixture is then diluted with 100 ml of diethyl ether,, and washed firstly with 20 ml of 2N hydrochloric acid and then with 2×30 ml of 5% strength sodium hydrogencarbonate solution. The organic phase is then dried over sodium sulfate and filtered, and the solvent is carefully stripped off under partial vacuum. Further purification for the next reaction step is unnecessary.

1-Ethyl-2-methyl-3-oxopropyl thioacetate

MS (EI, 70 eV): 174 ($M^+$ 0.5), 131 (17), 103 (12), 70 (32), 69 (12), 61 (11), 43 (100), 41 (20)

2.2. Acetalation of 1-ethyl-2-methyl-3-oxopropyl thioacetate with ethylene glycol 10 g (57 mmol) of the compound as prepared above are boiled with 7.01 g (114 mmol) of ethylene glycol, 150 mg of p-toluenesulfonic acid and 300 ml of toluene for 3 hours with reflux at the water separator.

The reaction mixture is then washed with 2×40 ml of saturated sodium hydrogencarbonate solution, dried over sodium sulfate and filtered, and the solvent is carefully stripped off under partial vacuum. Further purification for the next reaction step is unnecessary.

2-(1,3-Dioxolan-2-yl)-1-ethylpropyl thioacetate

MS (EI, 70 eV): No $M^+$, 175 (1), 148 (12), 101 (4), 74 (4), 73 (100), 45 (15), 43 (17)

2.3. Hydrolysis of 2-(1,3-dioxolan-2-yl)-1-ethylpropyl thioacetate 5 g (23 mmol) of 2-(1,3-dioxolan-2-yl)-1-ethylpropyl thioacetate are slowly added dropwise to 115 ml of 0.5N sodium hydroxide solution and 200 ml of methanol at room temperature in a stirred apparatus. The reaction mixture is then stirred for a further 18 hours at room temperature.

When the reaction is complete, the methanol is removed under partial vacuum and byproducts are removed by extraction of the aqueous solution with 100 ml of diethyl ether. 2N Hydrochloric acid is then used to acidify the mixture to pH 1, and the mercaptoacetal is extracted with diethyl ether (4×50 ml). The combined organic phases are washed with 30 ml of saturated sodium hydrogencarbonate solution, dried over sodium sulfate and filtered, and the solvent is carefully stripped off under partial vacuum. The 2-(1,3-dioxolan-2-yl)pentane-3-thiol has a purity of >95% (GC).

2-(1,3-Dioxolan-2-yl)pentane-3-thiol

MS (EI, 70 eV): 176 ($M^+$ 0.3), 143 (6), 113 (5), 74 (4), 73 (100), 45 (20), 41 (8)

EXAMPLE 3

Sensory Testing of the Selected Compound According to the Invention

3-Mercapto-2-methylpentanal 3.1. Concentration: 0.1 ppm Odor: meaty Taste: meaty, reminiscent of meat broth, reminiscent of cooked meat.

3.2. Odor threshold value: very low

EXAMPLE 4

Spectroscopic Data for a Selected Compound According to the Invention

3-Mercapto-2-methylpentanal

FTIR (gas phase): diastereomer 1: 2977 (m), 2942 (m), 2890 (m), 2809 (w), 2708 (m), 1739 (s), 1460 (w), 1387 (w), 1305 (w); diastereomer 2: 2976 (m), 2942 (m), 2890 (m), 2808 (w), 2706 (m), 1740 (s), 1461 (w), 1386 (w), 1307 (w)

w=weak, m=medium, s=strong bands

Figure 2:
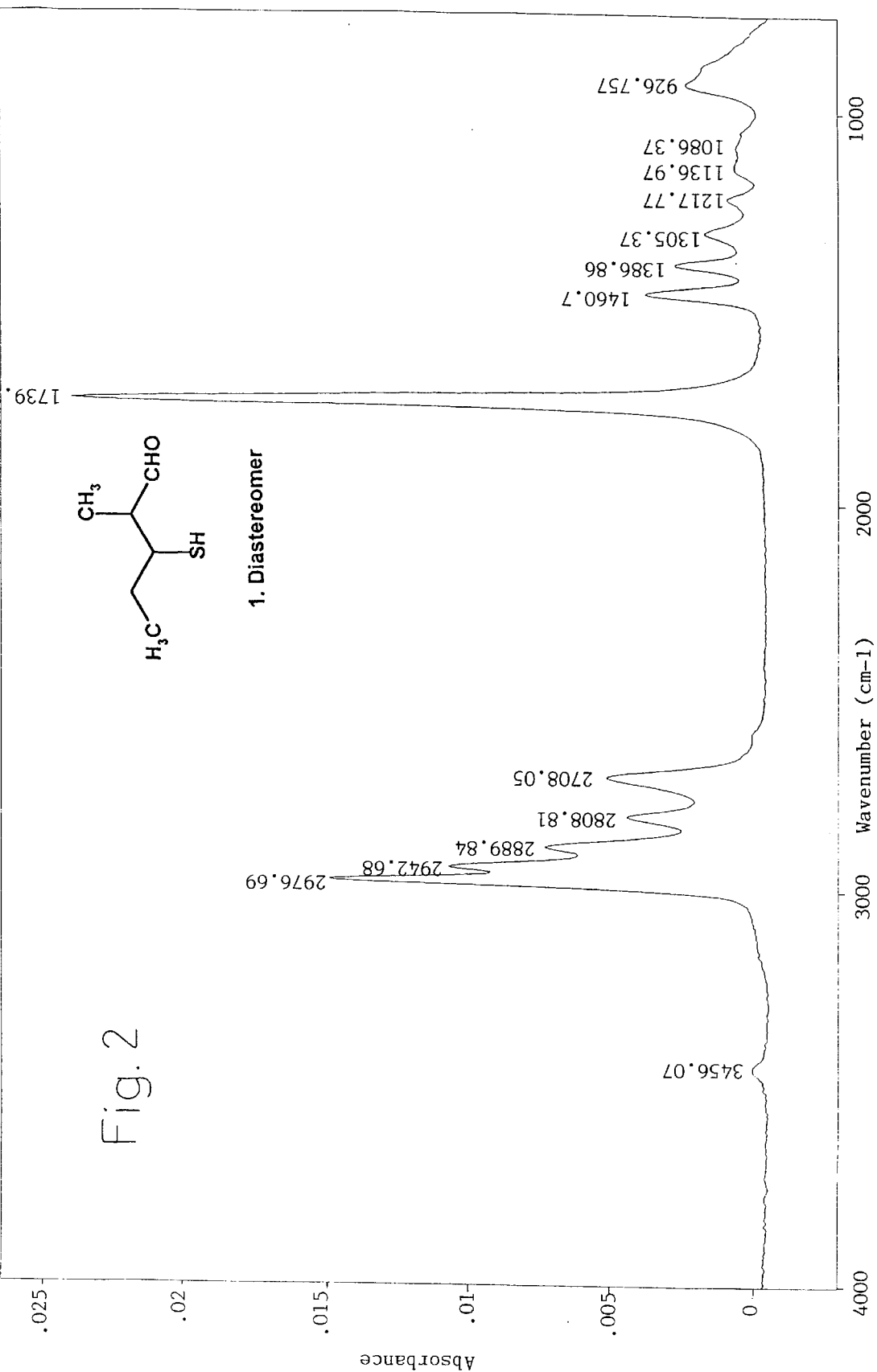

The spectra as in FIGS. 1 and 2 correspond to this data.

MS (EI, 70 eV): diastereomer 1: 132 ($M^+$, 12), 114 (13), 99 (30), 75 (33), 70 (100), 61 (24), 55 (82), 43 (39), 41 (97); diastereomer 2: 132 ($M^+$, 13) 114 (18); 99 (41), 75 (39), 70 (75), 61 (24), 55 (67), 43 (43), 41 (100)

The spectra as in FIGS. 3 and 4 correspond to this data.

What is claimed is:

1. Compound of the following formula A

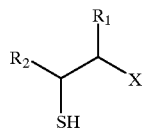

where

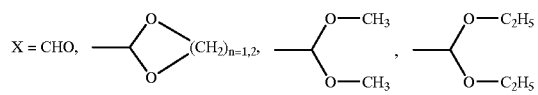

$R_1=CH_3$, $C_2H_5$, $C_3H_7$ (n, iso) or $C_4H_9$ (n, iso, tert) and
$R_2=CH_3$, $C_2H_5$, $C_3H_7$ (n, iso) or $C_4H_9$ (n, iso, tert).

2. A process for the production of 3-mercapto-2-alkyl-alkanal of the general formula A:

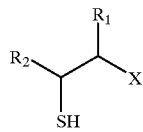

in which
X=CHO
$R_1=CH_3$, $C_2H_5$, $C_3H_7$ (n, iso) or $C_4H_9$ (n, iso, tert) and
$R_2=CH_3$, $C_2H_5$, $C_3H_7$ (n, iso) or $C_4H_9$ (n, iso, tert)
comprising reacting the corresponding 2-alkyl-2alkenal with hydrogen sulfide.

3. A process for the organoleptic modification of a material, said process comprising adding to said material of a compound of formula (A):

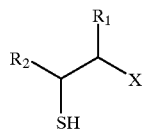

where

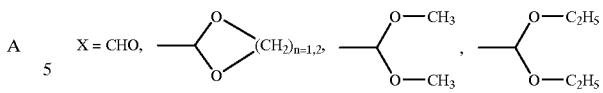

$R_1=CH_3$, $C_2H_5$, $C_3H_7$ (n, iso) or $C_4H_9$ (n, iso, tert) and
$R_2=CH_3$, $C_2H_5$, $C_3H_7$ (n, iso) or $C_4H_9$ (n, iso, tert).

4. A fragrance or flavor formulation, comprising a compound of formula (A):

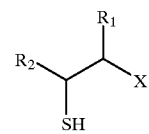

where

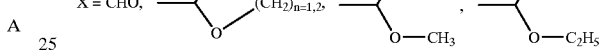

$R_1=CH_3$, $C_2H_5$, $C_3H_7$ (n, iso) or $C_4H_9$ (n, iso, tert) and
$R_2=CH_3$, $C_2H_5$, $C_3H_7$ (n, iso) or $C_4H_9$ (n, iso, tert).

5. A flavored foodstuff, comprising a compound of formula (A):

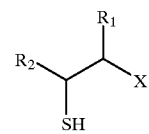

where

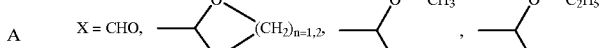

$R_1=CH_3$, $C_2H_5$, $C_3H_7$ (n, iso) or $C_4H_9$ (n, iso, tert) and
$R_2=CH_3$, $C_2H_5$, $C_3H_7$ (n, iso) or $C_4H_9$ (n, iso, tert).

* * * * *